United States Patent
Constantineau et al.

(10) Patent No.: US 8,814,831 B2
(45) Date of Patent: Aug. 26, 2014

(54) BALLISTIC MICRONEEDLE INFUSION DEVICE

(75) Inventors: Cole Constantineau, Cambridge, MA (US); Ryan Schoonmaker, San Marcos, CA (US); Michel Bruehwiler, Newton, MA (US); Eric Bené, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/303,027

(22) Filed: Nov. 22, 2011

(65) Prior Publication Data

US 2012/0143136 A1    Jun. 7, 2012

Related U.S. Application Data

(60) Provisional application No. 61/344,970, filed on Nov. 30, 2010.

(51) Int. Cl.
*A61M 5/178* (2006.01)
*A61M 5/158* (2006.01)
*A61M 5/142* (2006.01)

(52) U.S. Cl.
CPC ....... *A61M 5/158* (2013.01); *A61M 2005/1585* (2013.01); *A61M 2005/14264* (2013.01)
USPC ............. 604/164.01; 604/164.04; 604/164.12

(58) Field of Classification Search
USPC ............ 604/117, 136–137, 156–157, 164.01, 604/164.04, 164.11, 164.12, 174, 180, 46
See application file for complete search history.

(56) References Cited

U.S. PATENT DOCUMENTS

| | | | |
|---|---|---|---|
| 3,857,382 A | 12/1974 | Williams, Jr. et al. |
| 3,918,355 A | 11/1975 | Weber |
| 3,963,380 A | 6/1976 | Thomas, Jr. et al. |
| 4,204,538 A | 5/1980 | Cannon |
| 4,490,141 A | 12/1984 | Lacko et al. |
| 4,685,902 A | 8/1987 | Edwards et al. |
| 4,723,947 A | 2/1988 | Konopka |
| 4,734,092 A | 3/1988 | Millerd |
| 4,755,173 A | 7/1988 | Konopka et al. |
| 5,176,662 A | 1/1993 | Bartholomew et al. |
| 5,226,899 A | 7/1993 | Lee et al. |
| 5,242,406 A | 9/1993 | Gross et al. |

(Continued)

FOREIGN PATENT DOCUMENTS

| | | |
|---|---|---|
| EP | 0 980 687 | 2/2000 |
| EP | 1 743 667 A2 | 1/2007 |

(Continued)

*Primary Examiner* — Theodore Stigell
(74) *Attorney, Agent, or Firm* — Roylance, Abrams, Berdo and Goodman, LLP

(57) ABSTRACT

An infusion set has a disposable inserter that can insert a needle at a controlled rate of speed to a depth to deliver insulin or other medicament to the upper 3 mm of skin surface, and a skin securing, adhesive layer to secure the skin surface at the insertion site such that the inserter that can insert a needle without a risk of tenting of the skin surface. Position of the inserted needle can be maintained by providing a separated inner and outer hub of the infusion set that can isolate the inserted needle from external forces such that the needle can be maintained at a depth to deliver insulin or other medicament to the upper 3 mm of skin surface during normal use.

29 Claims, 9 Drawing Sheets

(56) References Cited

U.S. PATENT DOCUMENTS

| | | |
|---|---|---|
| 5,257,980 A | 11/1993 | Van Antwerp et al. |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,593,390 A | 1/1997 | Castellano et al. |
| 5,728,074 A | 3/1998 | Castellano et al. |
| 5,800,420 A | 9/1998 | Gross et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,925,021 A | 7/1999 | Castellano et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,110,148 A | 8/2000 | Brown et al. |
| 6,123,690 A | 9/2000 | Mejslov |
| 6,132,400 A | 10/2000 | Waldenburg |
| 6,175,752 B1 | 1/2001 | Say et al. |
| 6,206,134 B1 | 3/2001 | Stark et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,706,159 B2 | 3/2004 | Moerman et al. |
| 6,723,072 B2 | 4/2004 | Mahoney et al. |
| 6,740,059 B2 | 5/2004 | Flaherty |
| 6,749,560 B1 | 6/2004 | Konstorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,890,319 B1 | 5/2005 | Crocker |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,029,455 B2 | 4/2006 | Flaherty |
| 7,052,251 B2 | 5/2006 | Nason et al. |
| 7,056,302 B2 | 6/2006 | Douglas |
| 7,064,103 B2 | 6/2006 | Pitner et al. |
| 7,070,580 B2 | 7/2006 | Nielsen |
| 7,083,597 B2 | 8/2006 | Lynch et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,214,207 B2 | 5/2007 | Lynch et al. |
| 7,226,278 B2 | 6/2007 | Nason et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,407,493 B2 | 8/2008 | Cane' |
| 7,496,392 B2 | 2/2009 | Alarcon et al. |
| 7,585,287 B2 | 9/2009 | Bresina et al. |
| 7,699,807 B2 | 4/2010 | Faust et al. |
| 7,713,258 B2 | 5/2010 | Adams et al. |
| 7,722,595 B2 | 5/2010 | Pettis et al. |
| 7,731,691 B2 | 6/2010 | Cote et al. |
| 7,736,338 B2 | 6/2010 | Kavazov et al. |
| 7,879,010 B2 | 2/2011 | Hunn et al. |
| 7,896,844 B2 | 3/2011 | Thalmann et al. |
| 8,152,769 B2 | 4/2012 | Douglas et al. |
| 8,152,771 B2 | 4/2012 | Mogensen et al. |
| 8,162,892 B2 | 4/2012 | Mogensen et al. |
| 8,172,803 B2 | 5/2012 | Morrissey et al. |
| 8,172,805 B2 | 5/2012 | Mogensen et al. |
| 8,221,359 B2 | 7/2012 | Kristensen et al. |
| 8,262,618 B2 | 9/2012 | Scheurer |
| 8,277,415 B2 | 10/2012 | Mounce et al. |
| 8,285,328 B2 | 10/2012 | Caffey et al. |
| 8,287,467 B2 | 10/2012 | List et al. |
| 8,287,516 B2 | 10/2012 | Kornerup et al. |
| 8,306,596 B2 | 11/2012 | Schurman et al. |
| 8,310,415 B2 | 11/2012 | Mclaughlin et al. |
| 8,313,468 B2 | 11/2012 | Geipel et al. |
| 2002/0040208 A1 | 4/2002 | Flaherty et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0044306 A1 | 3/2004 | Lynch et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0158207 A1* | 8/2004 | Hunn et al. ............... 604/164.01 |
| 2004/0162521 A1 | 8/2004 | Bengtsson |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245799 A1 | 11/2005 | Brauker et al. |

(56) References Cited

U.S. PATENT DOCUMENTS

| | | |
|---|---|---|
| 2005/0273076 A1 | 12/2005 | Beasley et al. |
| 2005/0283144 A1 | 12/2005 | Shiono et al. |
| 2006/0001551 A1 | 1/2006 | Kraft et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0173410 A1 | 8/2006 | Moberg et al. |
| 2006/0178633 A1 | 8/2006 | Garibotto et al. |
| 2006/0200073 A1 | 9/2006 | Radmer et al. |
| 2006/0217663 A1 | 9/2006 | Douglas |
| 2006/0263839 A1 | 11/2006 | Ward et al. |
| 2006/0264835 A1 | 11/2006 | Nielsen et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0027427 A1 * | 2/2007 | Trautman et al. ............... 604/46 |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1 | 4/2007 | Richards |
| 2007/0093754 A1 | 4/2007 | Mogensen et al. |
| 2007/0118405 A1 | 5/2007 | Campbell et al. |
| 2007/0149925 A1 | 6/2007 | Edwards et al. |
| 2007/0191702 A1 | 8/2007 | Yodfat et al. |
| 2007/0219496 A1 | 9/2007 | Kamen et al. |
| 2008/0004515 A1 | 1/2008 | Jennewine |
| 2008/0021395 A1 | 1/2008 | Yodfat et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0103483 A1 | 5/2008 | Johnson et al. |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0281297 A1 | 11/2008 | Pesach et al. |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2008/0319414 A1 | 12/2008 | Yodfat et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0062767 A1 | 3/2009 | Van Antwerp et al. |
| 2009/0076453 A1 | 3/2009 | Mejlhede et al. |
| 2009/0124979 A1 | 5/2009 | Raymond et al. |
| 2009/0198191 A1 | 8/2009 | Chong et al. |
| 2009/0198215 A1 | 8/2009 | Chong et al. |
| 2009/0204077 A1 | 8/2009 | Hasted et al. |
| 2009/0221971 A1 | 9/2009 | Mejlhede et al. |
| 2009/0240240 A1 | 9/2009 | Hines et al. |
| 2009/0254041 A1 | 10/2009 | Krag et al. |
| 2009/0281497 A1 | 11/2009 | Kamen et al. |
| 2009/0326457 A1 | 12/2009 | O'Connor |
| 2010/0049129 A1 | 2/2010 | Yokoi et al. |
| 2010/0160902 A1 | 6/2010 | Aeschilimann et al. |
| 2010/0217105 A1 | 8/2010 | Yodfat et al. |
| 2010/0222743 A1 | 9/2010 | Frederickson et al. |
| 2010/0286714 A1 | 11/2010 | Gyrn et al. |
| 2010/0291588 A1 | 11/2010 | Mcdevitt et al. |
| 2010/0298830 A1 | 11/2010 | Browne et al. |
| 2012/0253282 A1 | 10/2012 | Nagel et al. |
| 2012/0259185 A1 | 10/2012 | Yodfat et al. |
| 2012/0265034 A1 | 10/2012 | Wisniewski et al. |
| 2012/0277554 A1 | 11/2012 | Schurman et al. |
| 2012/0277667 A1 | 11/2012 | Yodat et al. |
| 2012/0277724 A1 | 11/2012 | Larsen et al. |
| 2012/0283540 A1 | 11/2012 | Brüggemann |
| 2012/0291778 A1 | 11/2012 | Nagel et al. |
| 2012/0293328 A1 | 11/2012 | Blomquist |
| 2012/0296269 A1 | 11/2012 | Blomquist |
| 2012/0296310 A1 | 11/2012 | Blomquist |
| 2012/0296311 A1 | 11/2012 | Brauker et al. |

FOREIGN PATENT DOCUMENTS

| | | |
|---|---|---|
| WO | WO 99-34212 | 7/1999 |
| WO | WO 2007-051139 | 5/2007 |
| WO | WO 2008/051920 A2 | 5/2008 |
| WO | WO 2009-021039 | 2/2009 |
| WO | WO 2009-021052 | 2/2009 |
| WO | WO 2010/085338 A1 | 7/2010 |

* cited by examiner

BALLISTIC MICRONEEDLE INFUSION DEVICE

CROSS-REFERENCE TO RELATED APPLICATIONS

This application claims the benefit under 35 U.S.C. §119 (e) of a U.S. provisional patent application of Cole Constantineau et al. entitled "Ballistic Microneedle Infusion Device", Ser. No. 61/344,970, filed on Nov. 30, 2010, the entire content of said application being incorporated herein by reference.

FIELD OF THE INVENTION

The present invention relates generally to infusion sets, including a disposable inserter for an infusion set, which ensures proper positioning of insertion by using an adhesive to hold an infusion set in position, and a ballistic inserter releasably coupled with the infusion set to insert a needle at a controlled rate of speed to a desired intradermal depth.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive which retains the base on the skin surface during use, which may be applied to the skin manually or with the aid of a manual or automatic insertion device.

Currently, most insulin infusion sets deliver insulin to the sub-cutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

Further, most insulin infusion sets typically do not provide any features to isolate the inserted needle from shock or other external forces. Since these infusion sets typically deliver insulin 4-10 mm below the skin surface, shock or other external forces have less effect on the deeper inserted needle. However, where an attempt is made to target the upper 3 mm of skin surface, any shock or movement of the set can adversely affect needle insertion and infusion performance.

Still further, most insulin sets have inserters that can result in skin surface "tenting" during needle insertion, where the skin surface is deflected somewhat prior to or during needle insertion which makes precisely targeting the upper 3 mm of skin surface difficult.

Accordingly, a need exists for an infusion set that can deliver content to the upper 3 mm of skin surface, the intradermal space, to facilitate better drug absorption, while maintaining a degree of comfort to the user.

SUMMARY OF THE INVENTION

An object of the present invention is to provide an infusion set which can deliver insulin or other medicament to the upper 3 mm of skin surface, the intradermal space, to facilitate better drug absorption, while maintaining a degree of comfort to the user.

Another object of the present invention is to provide an infusion set having a disposable inserter that can insert a needle at a depth to deliver insulin or other medicament to the upper 3 mm of skin surface.

Another object of the present invention is to provide an infusion set having a disposable inserter that can insert a needle at a controlled high rate of speed to substantially reduce tenting of the skin surface and insert a needle at a depth to deliver insulin or other medicament to the upper 3 mm of skin surface.

Another object of the present invention is to provide an infusion set having a disposable inserter that can be removed, thereby leaving a low-profile infusion set at the infusion site.

Another object of the present invention is to provide an infusion set having a skin securing, adhesive layer to secure the skin surface at the insertion site such that the inserter that can insert a needle without a risk of tenting of the skin surface.

Another object of the present invention is to provide an infusion set that can isolate an inserted needle from external forces such that the needle can be maintained at a depth to deliver insulin or other medicament to the upper 3 mm of skin surface during normal use.

These and other objects are substantially achieved by providing an infusion set having a disposable inserter that can insert a needle at a controlled high rate of speed to a depth to deliver insulin or other medicament to the upper 3 mm of skin surface, and a skin-securing adhesive layer to secure the skin surface at the insertion site such that the inserter that can insert a needle without a risk of tenting of the skin surface. The disposable inserter can be removed, thereby leaving a low-profile infusion set at the infusion site. The position of the inserted needle can be maintained by providing an inner and outer hub of the infusion set that can isolate the inserted needle from external forces such that the needle can be maintained at a depth to deliver insulin or other medicament to the upper 3 mm of skin surface during normal use.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

The exemplary embodiments of the present invention deliver insulin or other medicament to the intradermal layers of the skin via a standard insulin pump or other similar device. By utilizing a disposable ballistic inserter, a skin securing adhesive, and an isolated inner hub, proper insertion and maintenance of the inserted needle in the intradermal space is ensured using a low profile set, while maintaining a degree of comfort to the user.

The exemplary embodiments of the present invention provide an exemplary infusion set having a disposable ballistic inserter that can insert a needle at a depth to deliver content to the upper 3 mm of skin surface. To do so, the exemplary embodiments comprise a disposable ballistic inserter that can insert a needle of an infusion set at a controlled high rate of speed to substantially reduce tenting of the skin surface and insert the needle at a depth to deliver insulin or other medicament to the upper 3 mm of skin surface. The disposable ballistic inserter can be removed, thereby leaving a low-profile infusion set at the infusion site. The infusion set is also provided with at least one skin securing, adhesive layer to secure the infusion set to the skin surface at the insertion site, such that the ballistic inserter when activated by the user is at the correct position relative to the skin surface, and such that the skin is secured during insertion to further aid needle insertion without a risk of tenting of the skin surface. The infusion set is still further provided with an inner and outer hub that can isolate an inserted needle from external forces such that the needle can be maintained at a depth to deliver content to the upper 3 mm of skin surface during normal use.

Figure 1:
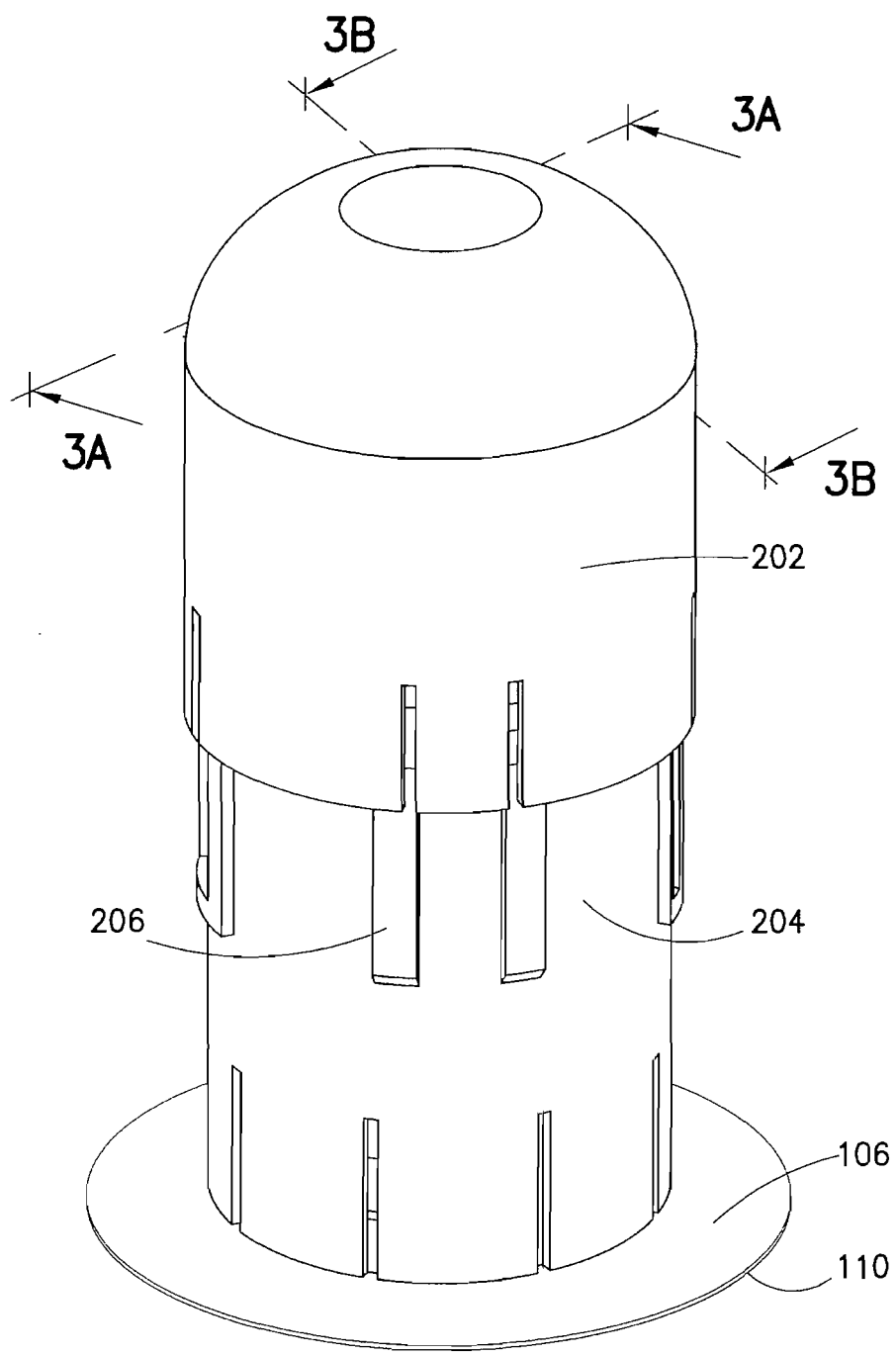
FIG. 1 is a perspective view of an infusion set and a disposable ballistic inserter in an assembled position in accordance with an embodiment of the present invention.
Figure 2:
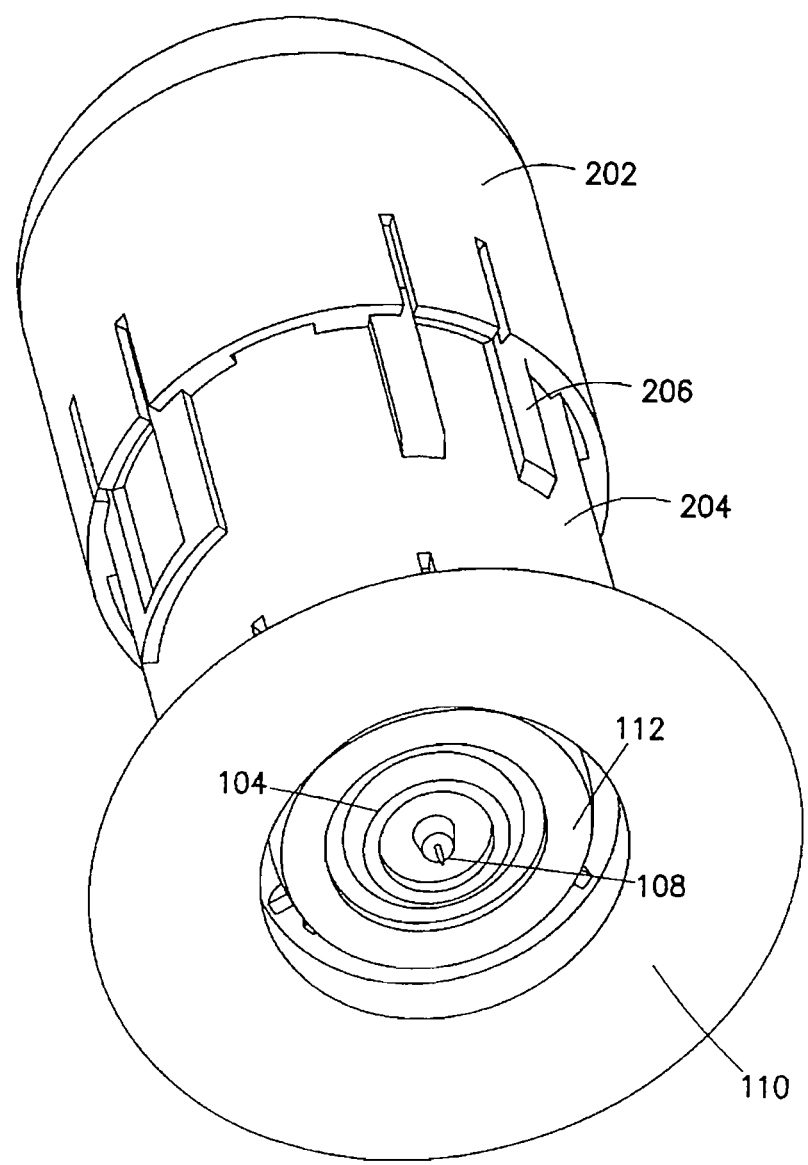
FIG. 2 is a bottom perspective view of the infusion set and disposable ballistic inserter of FIG. 1 in accordance with an embodiment of the present invention.
Figure 3A:
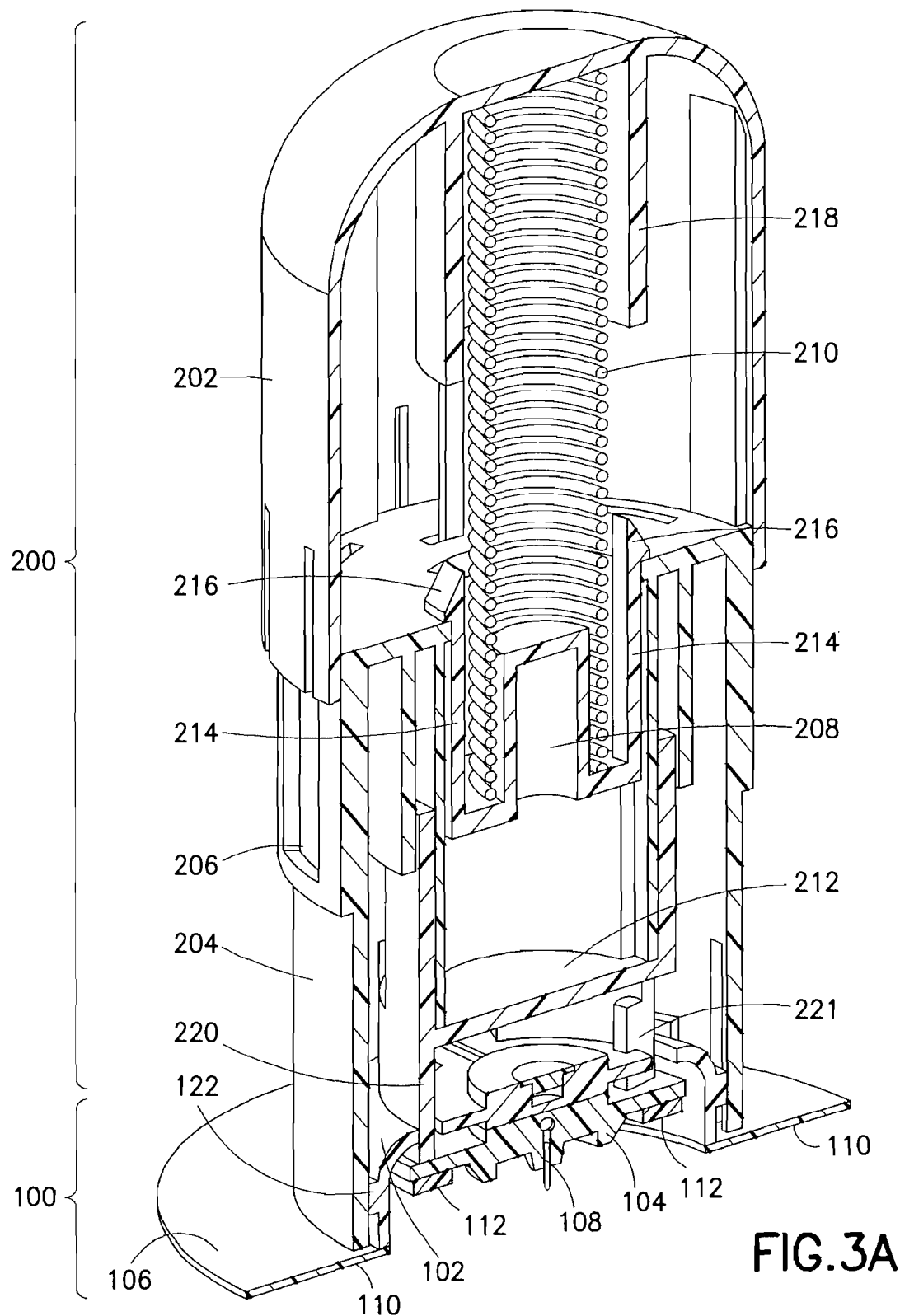
FIG. 3A is a cross-sectional view of the infusion set and disposable ballistic inserter of FIG. 1 prior to activation, in accordance with an embodiment of the present invention.

FIGS. 1 and 2 are perspective views of an infusion set and a disposable ballistic inserter in an assembled configuration in accordance with an embodiment of the present invention, and FIG. 3A is a cross-sectional view of the infusion set and disposable ballistic inserter of FIG. 1 prior to activation. In a preferred embodiment, the infusion set and disposable ballistic inserter are received by the user in the assembled configuration, but embodiments of the present invention are not limited thereto.

As shown in FIGS. 1, 2 and 3A, the infusion set 100 is releasably secured to the disposable ballistic inserter 200 for placement of the infusion set and insertion of a needle or cannula into a skin surface. To do so, the infusion set 100 can comprise an outer hub 102, an inner hub 104 (i.e., needle hub), and a surrounding member 106. The inner hub 104 can comprise at least one needle 108. The needle 108 can preferably comprise a 34 gauge, single-bevel stainless steel needle/cannula, but embodiments are not limited thereto. In yet other embodiments of the present invention, the needle 108 can be plastic or other material, between 25 gauge and 36 gauge, and be provided with a tri-bevel or 5-bevel, and be between 1.0 and 10 mm long, but embodiments are not limited thereto. The needle 108 can be bonded to the inner hub 104 with an adhesive, such as a Loctite/UV cured adhesive, or can be over molded with, or threaded into the inner hub 104. The surrounding member 106 can comprise an outer skin adhesive 110, and the inner hub 104 can comprise an inner skin adhesive 112. In exemplary embodiments of the present invention described below, the hubs and other elements can be constructed of a molded plastic material, polycarbonate, thermoplastic polymer such as polyethylene terephthalate (PET and PETG), or similar materials.

Figure 4:
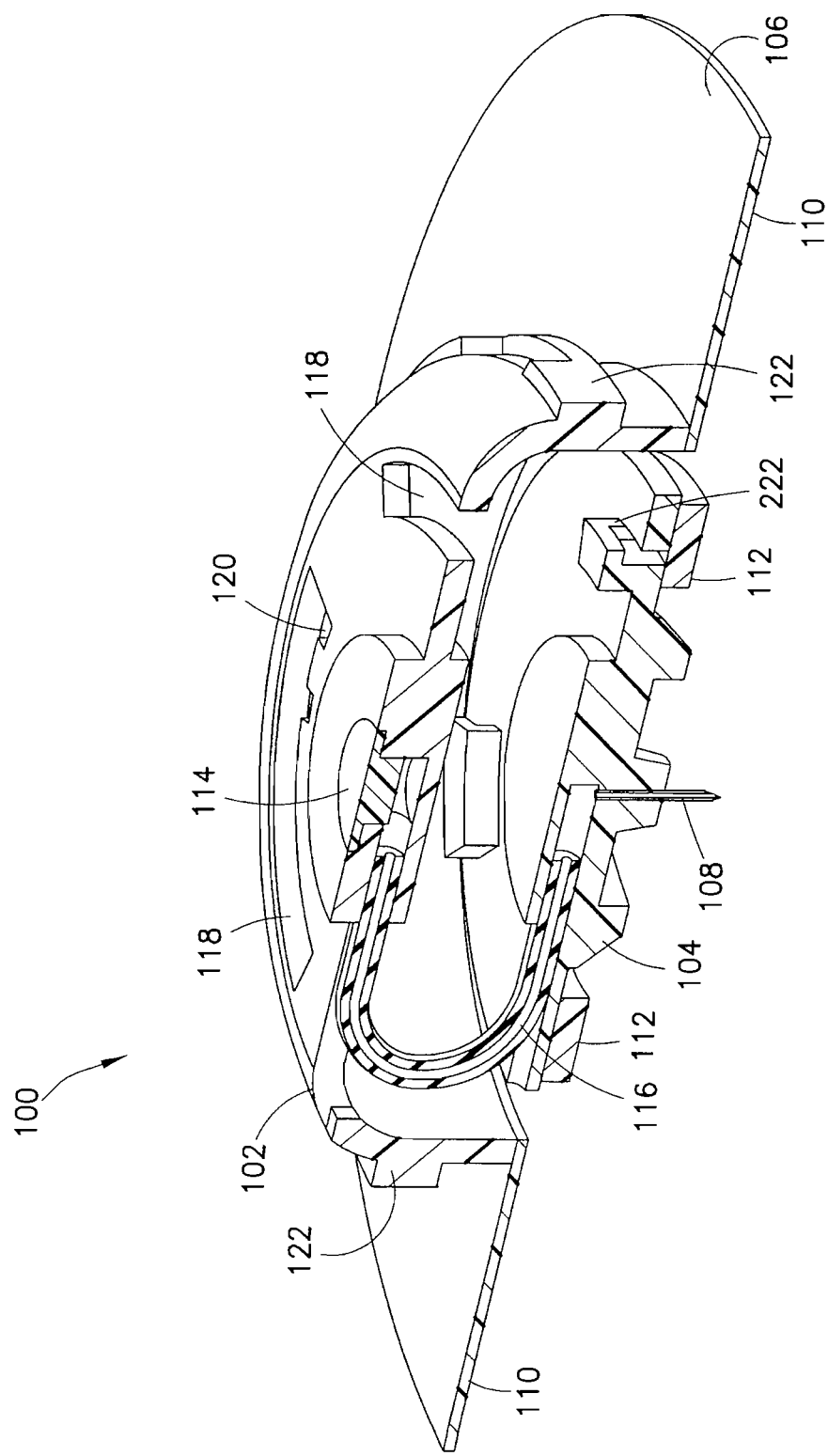
FIG. 4 is a cross-sectional view of the infusion set after activation and removal of the disposable ballistic inserter but prior to attachment to the infusion pump tube attachment, in accordance with an embodiment of the present invention.

As shown in greater detail in FIG. 4, the outer hub 102 of the infusion set 100 comprises a low-profile, substantially circular, dome shape with rounded edges and a number of features to releasably secure the ballistic inserter 200 and after removal thereof, releasably secure a tube set connection. To do so, the upper surface of the outer hub 102 comprises a septum/valve connection 114 for connection with a tube set connector after removal of the ballistic inserter 200. The connection 114 is connected to the inner hub 104 via at least one flexible tubing 116. In an exemplary embodiment of the present invention, the inner hub 104 is connected to the outer hub 102 solely through the flexible tubing 116 after removal of the ballistic inserter 200. Prior to insertion, the inner hub 104 is held within the outer hub 102 by a table 212 as described in greater detail below. After activation, the inner hub 104 is held in place by the inner skin adhesive 112, and is connected to the outer hub 102 through the flexible tubing 116.

As further shown in FIG. 4, the outer hub 102 has a diameter which can releasably fit within an opening of the ballistic inserter 200 as described in greater detail below. The upper surface of the outer hub 102 still further comprises one or more arcuate openings 118 positioned over the inner hub 104. In doing so, arms 220 of the table 212 of the ballistic inserter 200 can pass through the outer hub 102 and contact and secure the inner hub 104. Further, the arcuate form of the openings 118 allow rotation of the arms 220 of the table 212, and one or more gaps 120 in the openings 118 can permit the arms of the table 212 to be pulled free from the outer hub 102 of the infusion set 100 and discarded as described in greater detail below.

The outer hub 102 still further comprises a stepped rail 122 around an outer circumference for releasably securing the ballistic inserter 200 to the infusion set 100. The stepped rail 122 is provided as a guidance feature to align travel in the normal direction after impact. Further, the stepped rail 122 comprises chamfers that are configured to allow the lower inserter housing 204 to be rotated clockwise as described in greater detail below. Rotating the lower inserter housing 204 causes attachment arms of the lower inserter housing 204 to flex out, thereby allowing the ballistic inserter 200 to be removed from the infusion set 100.

Returning to FIGS. 1, 2 and 3A, the ballistic inserter 200 comprises a button 202 slidably coupled to a lower inserter housing 204. The button 202 is configured to slidably engage the lower inserter housing 204 as guided by one or more tracks 206 on an outer surface of the lower inserter housing 204. A ballistic hammer 208 is captured within the assembled button 202 and lower inserter housing 204, and is configured to be driven downward by a spring 210. The table 212 is positioned within the lower inserter housing 204 to extend through the outer hub 102 of the infusion set 100 as described above, and to contact and secure the inner hub 104. Prior to insertion, the inner hub 104 is held within the outer hub 102 by the table 212. To do so, the table 212 is releasably locked to the inner hub 104 via one or more arms 220 which protrude through openings 118 of the outer hub 102, and capture detents 222 on an upper surface of the inner hub 104. The arms 220 of the table 212 can be released from the detents 222 of the inner hub 104 by a twisting motion as described in greater detail below.

The button 202 captures the spring 210 between a closed upper button surface within member 218 and the hammer 208. In doing so, the spring 210 is configured to urge the hammer 208 downward upon loading and release of the hammer. However, prior to activation, the hammer 208 is held from downward movement by one or more aims 214 and inclined detents 216 thereon, held by an opening in the lower inserter housing 204.

Figure 3B:
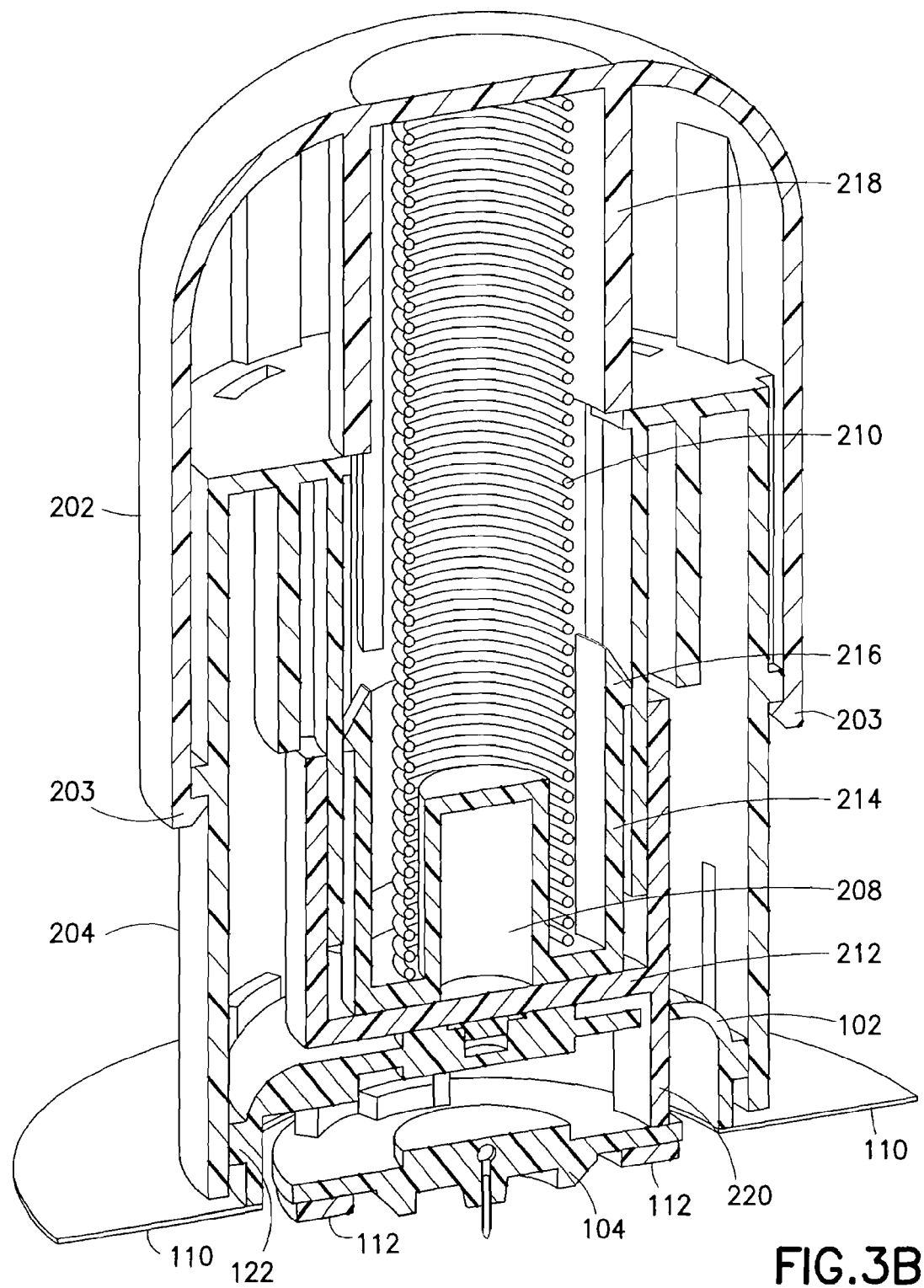
FIG. 3B is a cross-sectional view of the infusion set and disposable ballistic inserter of FIG. 1 after activation, in accordance with an embodiment of the present invention.

Accordingly, downward movement of the button 202 serves to first compress the spring 210. At or near an end of downward travel of the button 202, member 218 of the button 202 contact the inclined detents 216 of the hammer 208, which releases the one or more arms 214 and inclined detents 216 from the opening in the lower inserter housing 204 and the hammer 208 is released and urged downward by the spring 210. The button 202 is then locked to the lower inserter housing 204 at this point via button snaps 203 capturing detents on the lower inserter housing 204 as shown in FIG. 3B.

Once released by the button 202, the hammer 208 is urged downward and strikes the table 212. The struck table 212 now moves downward and the arms 220 of the table 212 extending through the outer hub 102 moves the inner hub 104 and needle 108 downward such that the inner hub 104 is placed at the infusion site, secured via adhesive 112, and needle 108 is inserted. In doing so, the inner hub 104 and needle 108 are driven into the skin surface at a controlled high rate of speed, of 3.3 ft/sec. (1.0 m/sec.) up to and including those greater than 10 ft/sec. (3.0 m/sec.), which minimizes the risk of tenting at needle insertion. By using such a driving spring, a high-speed insertion is achieved which is considered more reliable for insertion of short (i.e., 1.5 mm) needle or cannula.

As noted above, precise insertion is achieved by first securing the infusion set 100 to the infusion site via the adhesive 110, which permits the user to activate the disposable ballistic inserter 200 at the proper alignment as described above, and insert the needle. In doing so, the needle is driven into the skin surface at a controlled high rate of speed to minimize the risk of tenting at needle insertion. Further, the adhesive 110 at or very near the insertion site secures the skin surface and further minimizes tenting of the skin surface during insertion.

After insertion, the user can then turn or twist the ballistic inserter 200 relative to the secured infusion set 100 for release. Specifically, the infusion set 100 is secured to the infusion site via the adhesive 110 and 112, which permits the user to turn the ballistic inserter 200 relative to the set 100 for release without affecting infusion set position, such that the rail 122 and openings 118 and 120 of the outer hub 102 allow the release and removal of the disposable ballistic inserter 200. Specifically, the arms 220 of the table member 212 of the ballistic inserter 200 pass through the outer hub 102 and contact and secure the inner hub 104. The table 212 is releasably locked to the inner hub 104 via arms 220 which protrude through openings 118 of the outer hub 102, and capture detents 222 on an upper surface of the inner hub 104. The arms 220 of the table 212 can be released from the detents 222 of the inner hub 104 by a twisting motion. The arcuate form of the openings 118 allow rotation of the arms 220 of the table 212, and gaps 120 in the openings 118 permit the arms 220 of the table 212 to be pulled free from the outer hub 102 of the infusion set 100. Further, rotating the lower inserter housing 204 causes attachment anus of the lower inserter housing 204 to flex out, thereby allowing the ballistic inserter 200 to be removed from the infusion set 100.

In an exemplary use of the embodiments of the present invention, proper insertion of the infusion set 100 into the delivery site consists of three straightforward steps. First, the infusion set 100 and ballistic inserter 200 are positioned and used to insert the needle 108 into the intradermal layers of the skin. To do so, an adhesive covering backing (not shown) if provided, can be peeled off one or both of the skin adhesive layers 110 and 112 of the infusion set 100, and the infusion set 100 is adhered to the skin surface in the area of the desired infusion site. The user then presses downward on the inserter button 202, loading the spring 208, releasing the hammer 208 to strike the table 212, which moves the inner hub 104, placing the inner hub 104 of the infusion set at the infusion site and inserting the needle 108 into the skin surface of the infusion site.

Figure 5:
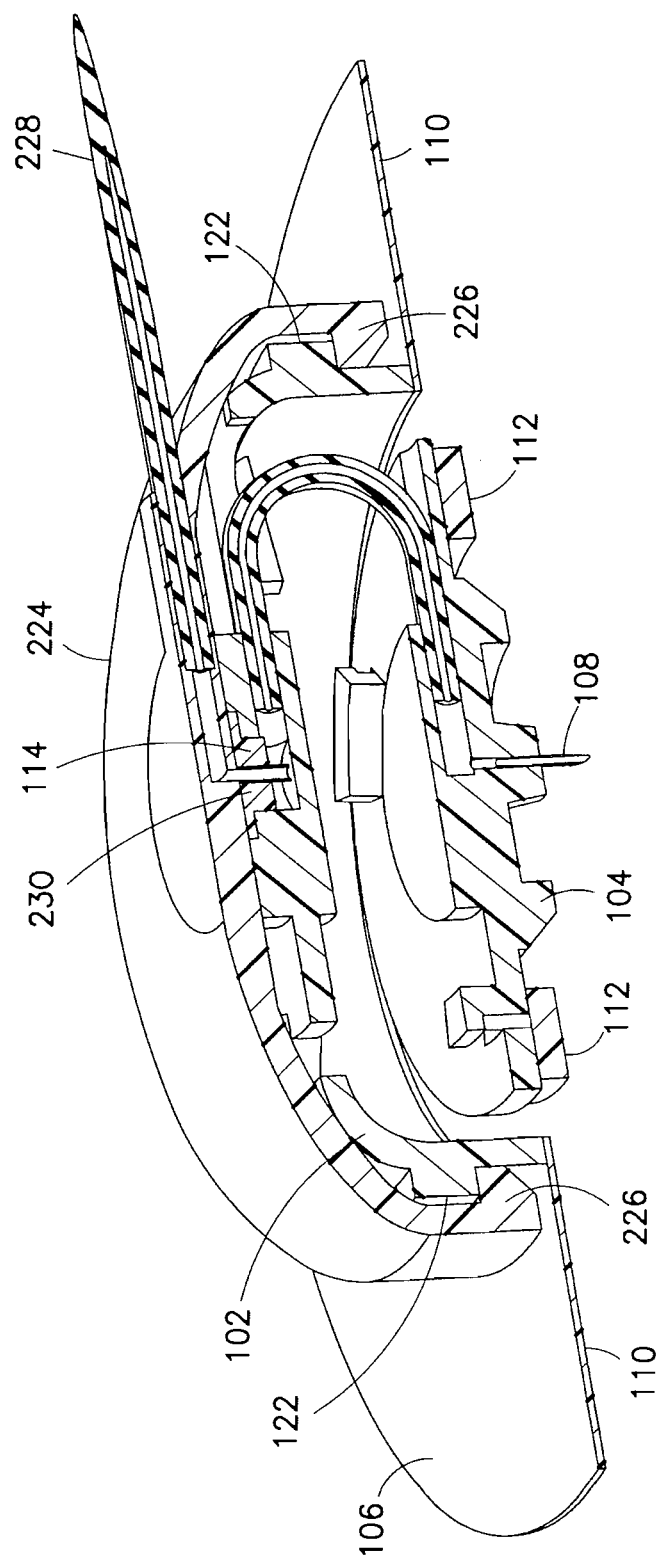
FIG. 5 is a cross-sectional view of the infusion set after activation and attachment to the infusion pump tube attachment, in accordance with an embodiment of the present invention.

Second, the ballistic inserter 200 is removed from the infusion set 100 with a twisting motion and then discarded, leaving the low-profile infusion set 100 in place. As shown in FIG. 4, the infusion set 100 is then exposed to receive the tube set connection (not shown). Once in position, the inner hub 104 is fully enclosed by the outer hub 102, and is connected to the outer hub 102 solely through the flexible tubing 116 after removal of the ballistic inserter 200. Further, the inner hub is adhesively secured to the skin surface using the adhesive layer 112 that is separate from the adhesive layer 110 securing the outer hub 102 to the skin surface. Third, the user can then attach the tube set connection as shown in FIG. 5 to the valve connection 114 of the outer hub 102 using one or more of the features used to secure the ballistic inserter 200 to the infusion set 100. FIG. 5 is a cross-sectional view of the infusion set after activation and attachment to the infusion pump tube attachment, in accordance with an embodiment of the present invention.

As shown in FIG. 5, the infusion pump tube attachment 224 can comprise a substantially dome-shaped component to cover, enclose and secure with the outer hub 102. To do so, the exemplary attachment 224 comprises a dome-shaped component having an opening to receive the outer hub 102, and includes connector snaps 226 to attach the infusion pump tube attachment 224 to the stepped rail 122 of the outer hub 102 similar to the connection with the ballistic inserter 200. Release of the infusion pump tube attachment 224 can also be performed in a manner similar to the release of the ballistic inserter 200, wherein a turning motion of the attachment 224 deflects the connector snaps 226 from the stepped rail 122 of the outer hub 102 and releases the infusion pump tube attachment 224. Further, the infusion pump tube attachment 224 can be provided with a connector needle or cannula 230 for piercing the septum/valve connection 114 of the outer hub 102, and can be provided with the tube 228 for connection with an infusion pump (not shown).

The user can prime the pump tube attachment 224 prior to attachment to the infusion set 100, and then deliver insulin or other medicament to the infusion site via the attached infusion pump (not shown).

Inside the exemplary device, the inner hub 104 is entirely contained within the outer hub 102, and the ballistic inserter 200 can be connected to the inner hub 104 through openings in the outer hub 102. As noted above, the ballistic inserter 200 comprises the button 202, spring 210, hammer 208 and table 212. Accordingly, as the user presses downward on the inserter button 202, the spring 210 is loaded up against the hammer 208, which is snapped to the lower inserter housing 204. When the spring 210 is fully compressed, the same downward motion unlatches the hammer snaps of arms 214, and the button 202 is locked into the lower inserter housing 204.

The spring 210 is compressed until it gains a maximum potential energy. This energy is determined by calculating the torsional stresses built up in the spring as it is compressed. By calculating potential energy, and the kinetic energy at the point of needle insertion, an insertion velocity can be calculated. In an exemplary embodiment of the present invention, the spring 210 is configured to insert an exemplary needle at a controlled high rate of speed, of 3.3 ft/sec. (1.0 m/sec.) up to and including those greater than 10 ft/sec. (3.0 m/sec.). Depending upon cannula sharpness, a high terminal velocity produces more reliable results for intradermal insertions of short (i.e., 1.5 mm) needle or cannula.

When the hammer snaps of arms 214 are unlatched, the hammer 208 is propelled downward by the spring 210 toward the table 212. The table 212 is releasably locked to the inner hub 104 via one or more arms 220 which protrude through the outer hub 102. When the hammer 208 collides with the table 212, the inner hub 104 moves downward, adheres to the skin surface, and pierces the skin surface with the needle 108.

Figure 6:
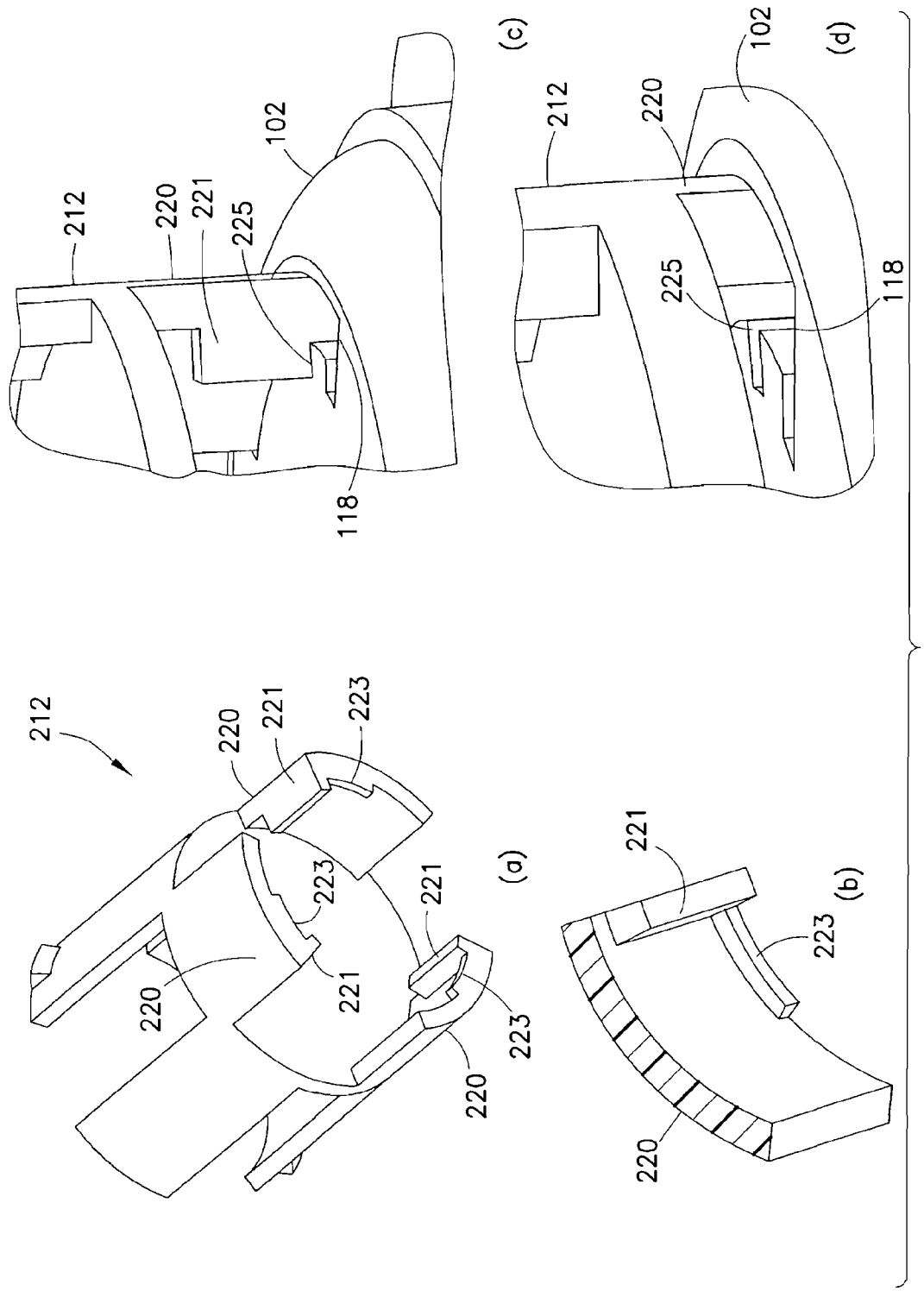
FIG. 6 is a set of enlarged views of the table of the infusion set of FIG. 1, in accordance with an embodiment of the present invention.

Prior to insertion, the table 212 prevents rotation of the ballistic inserter 200 with respect to the outer hub 102. FIG. 6 is a set of enlarged views of the table of the infusion set of FIG. 1, in accordance with an embodiment of the present invention. As shown in FIG. 6(a), the table 212 comprises on or more arms 220 having a number of features thereon. For example, the arms 220 comprise a vertical face member 221 to prevent rotation relative to the outer hub 102 before insertion as shown in FIG. 6(c). The members 221 are caught by openings 225 in the outer hub 102. After insertion, members 221 are below openings 225 in the outer hub 102, such that the table 212 is free to rotate relative to the outer hub 102 as shown in FIG. 6(d). The anus 220 further comprise one or more undercuts 223 which are configured to capture the detents 222 on the upper surface of the inner hub 104. The arms 220 of the table 212 can be released from the detents 222 of the inner hub 104 after insertion, by the same twisting motion that releases the lower inserter housing 204 from the set as described above.

Figure 7:
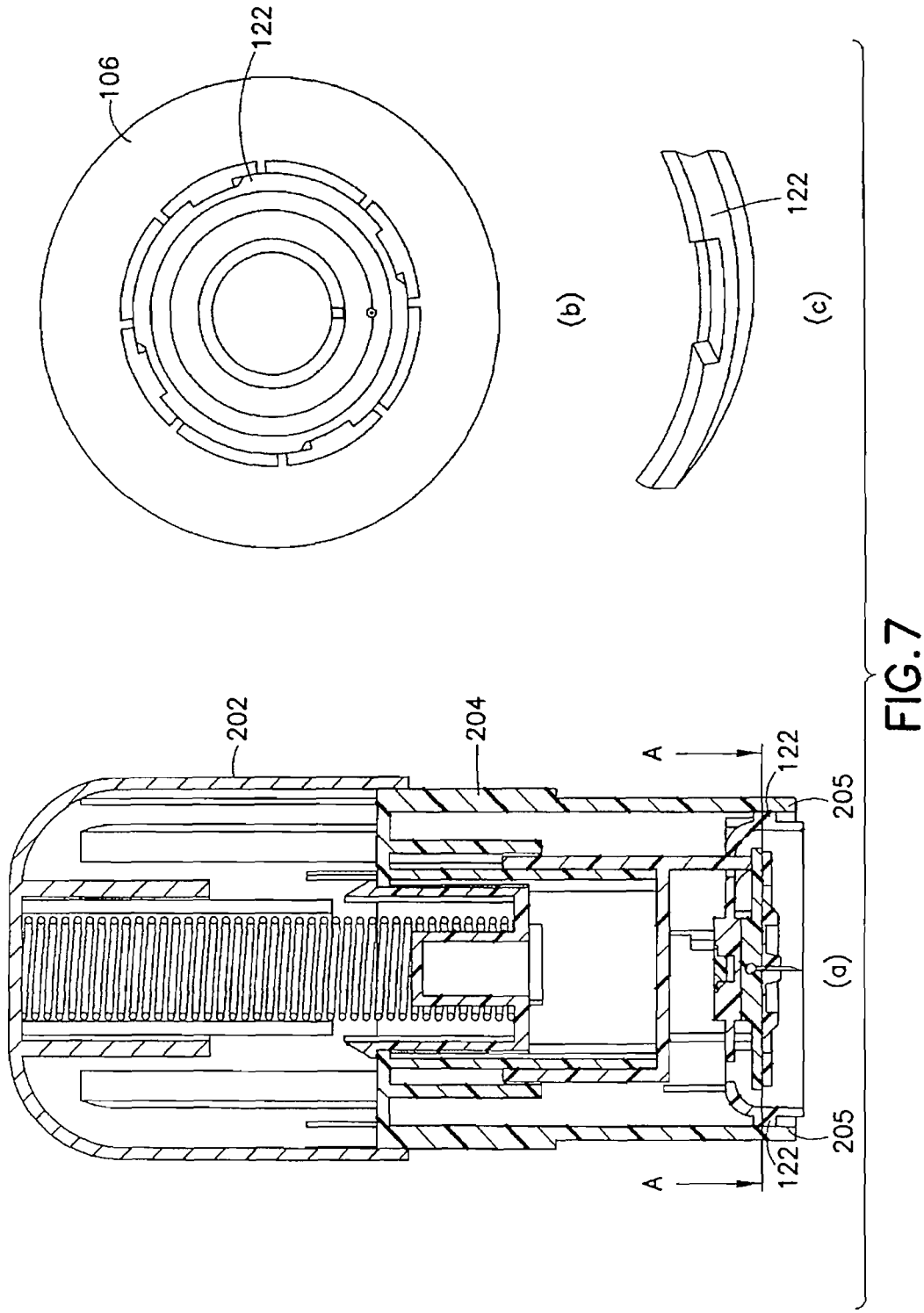
FIG. 7 is a set of enlarged sectional views of the lower inserter housing of the disposable ballistic inserter and the infusion set, in accordance with an embodiment of the present invention.
Figure 8:
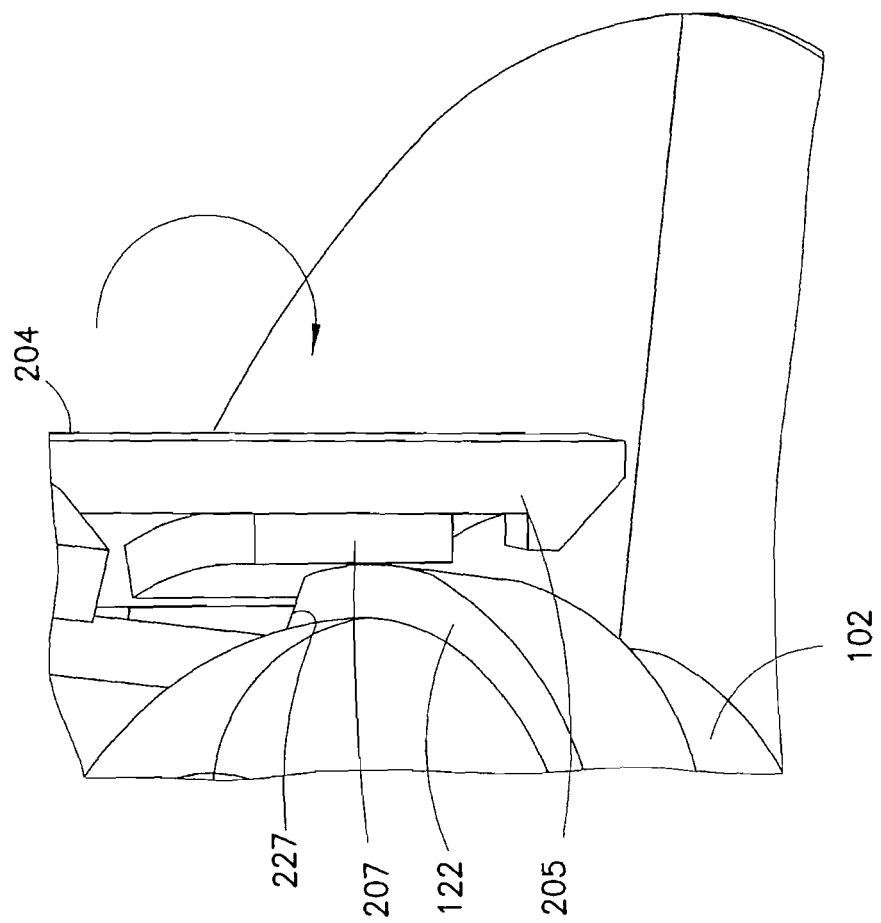
FIG. 8 is an enlarged view of the lower inserter housing of the disposable ballistic inserter being deflected away and released from the infusion set, in accordance with an embodiment of the present invention.

After the needle 108 is inserted, and the table 212 and inner hub 104 are in a down position, the user can turn the ballistic inserter 200 (e.g., clockwise), and the table 212 rotationally slides away from the inner hub 104 which is locked to the skin surface via the adhesive layer 112. This turning motion also flexes the lower inserter housing 204 snaps 205 outward, away from the outer hub 102. As described above and shown in FIGS. 7(a), 7(b) and 7(c), and in FIG. 8, the outer hub 102 comprises the stepped rail 122 with chamfers around an outer circumference for releasably securing the ballistic inserter 200 to the infusion set 100, and for later releasably securing the infusion pump tube attachment 224 with the outer hub 102. To do so, the lower inserter housing 204 comprises attachment arms with snaps 205 for securing the lower inserter housing 204 to the rail 122 of the outer hub 102. The lower inserter housing 204 further comprises elements 207 which are configured to engage the chamfers 227 of the rail 122. In doing so, the stepped rail 122 is configured to allow the lower inserter housing 204 to be rotated (e.g., clockwise) which causes the attachment arms of snaps 205 of the lower inserter housing 204 to flex out as urged by contact with the chamfers 227 of the rail 122, thereby allowing the inserter 200 to be removed from the set 100. The user can now pull off the ballistic inserter 200 for disposal.

Accordingly, a simple rotational and vertical motion can be used to release the ballistic inserter 200. Potentially, a rotational unlocking motion can cause an infusion set to peel off the skin surface if the user twists the entire assembly at an angle. Disconnecting the ballistic inserter 200 from the outer hub 102 after the down stroke of the button 202 minimizes this risk, and is more ergonomic and reliable.

To ensure shock isolation of the inner hub 104, the inner hub 104 is fully enclosed by the outer hub 102, and is connected to the outer hub 102 solely through the flexible tubing 116 after removal of the ballistic inserter 200. Further, the inner hub is adhesively secured to the skin surface using the adhesive layer 112 that is separate from the adhesive layer 110 securing the outer hub 102 to the skin surface. The inner hub 104 has a separate adhesive, and is connected to the outer hub 102 via only the flexible tube 116, such that the inner hub 104 is protected from external vibrations and forces. In the exemplary embodiment shown, the flexible tubing 116 at least partially loops upward (on the vertical) between the inner hub 104 and the outer hub 102, which permits a smaller footprint device profile. As noted above, the inner hub 104 is connected to the outer hub 102 solely through the flexible tubing 116. Prior to insertion, the inner hub 104 is held within the outer hub 102 by the table 212. After activation and release and removal of the table 212, the inner hub 104 is held in place by the inner skin adhesive 112 beneath the inner hub 104, and is connected to the outer hub 102 through the flexible tubing 116. The tube set connection 224 can then be snapped over the same features which held the ballistic inserter 200, and rotated to allow for comfortable pump tube routing.

In the disclosed arrangement, the needle 108 is protected from external forces and vibrations by the outer hub 102, and the isolation of the inner hub 104. By carefully isolating the inner hub 104 and the needle 108 from external forces, the needle position within the intradermal layer is maintained.

Further, the arrangement of the assembled set 100 and ballistic inserter 200 ensure proper alignment and positioning. Most existing inserters are either oversized, to ensure an insertion force perpendicular to the skin surface, or are thin and portable, which can lead to misaligned insertion. In the exemplary embodiments of the present invention, by first adhering or "locking" the outer skin adhesive 110 of the infusion set 100 to the skin surface, the ballistic inserter 200 is aligned properly for needle insertion. Accordingly, the exemplary embodiments of the present invention can include a relatively small inserter which is properly aligned with the infusion site at a time of use.

Such a system and method further allows the use of a small intradermal needle, or microneedle, which can be placed perpendicular to the skin surface, and which is isolated from outside forces, thereby maintaining position and causing less pain to the user during use. Still further, by infusing into the intradermal layer of the skin, the exemplary embodiments of the present invention offer the potential for better absorption of insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

As noted above, intradermal infusion sets are at risk of tenting, which is the undesired effect where skin is deflected at or during insertion, creating a shape associated with a tent. In doing so, the skin surface tents during needle insertion rather than needle penetration into the skin. However, since the present invention provides a needle which is inserted at a controlled high rate of speed, of 3.3 ft/sec. (1.0 m/sec.) up to and including those greater than 10 ft/sec., and wherein the skin surface is secured at and/or near the insertion site, the exemplary embodiments of the present invention do not present such a risk and ensure more precise needle insertion depth.

In existing steel cannula infusion sets which deliver insulin to the subcutaneous layer, the needle is not isolated from any undesired outside forces which may cause pain when translated to the needle and the needle moves within the skin. Also, other intradermal devices face problems of premature or otherwise undesired needle removal when the device is bumped if the needle is not isolated form the outside forces.

In the exemplary embodiments of the present invention, the intradermal needle is isolated from outside forces by at least three features. First, the outer hub 102 shields the sensitive inner hub 104 from direct contact with external forces. Second, the inner hub 104 and outer hub 102 are secured to the infusion site via separate adhesive segments. Third, the connection between the outer hub 102 and the inner hub 104 is extremely flexible, so that any forces imparted on the protective outer hub 102 do not carry over to the needle 108. For example, the provision of the flexible tubing connection 116, along with the outer hub 102, serves to effectively isolate the needle 108 from the outside forces and other interference.

Proper inserter alignment is accomplished by providing a solid, fixed foundation for the user to press the inserter button. Such a solid, fixed foundation is provided by the surrounding member 106, outer skin adhesive 110, and the inner skin adhesive 112 The skin adhesive layers secure the set 100 at a desired orientation, such that the attached ballistic inserter 200 is also at a desired orientation of use, and the user is substantially prevented from holding the inserter at angles to the insertion site. Accordingly, precise, repeatable insertions are accomplished via the pre-adhesion of the outer hub 102. By fixing a ring of skin around the actual insertion site, movement of the skin surface relative to the inner hub are reduced.

Existing infusion sets sometimes require the use of a separate inserter. In the exemplary embodiments of the present invention described herein, the user does not have to carry a separate inserter or load the infusion set onto an inserter. The integrated system allows the user more freedom from carrying and loading a separate inserter resulting in improved convenience and simpler operation.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion system, comprising:
    an infusion set, comprising an inner hub and an outer hub wherein at least one of said inner hub and said outer hub is releasably secured by an inserter; and
    an inserter comprising an inserter button and a spring, wherein said inserter button is configured to release said spring to move toward said infusion set and thereafter begin to drive said infusion set for placement at an infusion site,
    wherein said inserter comprises a hammer, disposed at an end of said spring and configured for release by movement of said inserter button, and a table, rotationally secured to said inner hub and configured to be struck by said hammer.

2. An infusion system as recited in claim 1, further comprising:
    a first adhesive layer disposed on a surface of said inner hub; and
    a second adhesive layer disposed on a surface of said outer hub, wherein said first adhesive layer is separate from said second adhesive layer.

3. An infusion system as recited in claim 1, further comprising a flexible tube coupled between said inner hub and said outer hub and providing a fluid communication path therebetween.

4. An infusion system as recited in claim 1, wherein said table is configured to releasably secure said inner hub in a retracted position within said outer hub.

5. An infusion system as recited in claim 1, wherein:
    said table comprises a first detent; and
    said inner hub comprises second detent, wherein said first detent is configured to rotationally engage with said second detent to releasably secure said table with said inner hub.

6. An infusion system as recited in claim 1, wherein said inserter further comprises a lower inserter housing, slidably coupled with said inserter button, and rigidly coupled with said outer hub.

7. An infusion system as recited in claim 6, wherein:
    said outer hub comprises a third detent; and
    said lower inserter housing comprises a fourth detent, wherein said third detent is configured to rotationally engage with said fourth detent to releasably secure said inserter with said outer hub.

8. An infusion system as recited in claim 1, wherein said spring is configured to place said infusion set at a controlled rate of speed, preferably greater than 3.3 ft/sec. (1.0 m/sec.).

9. An infusion system to insert and maintain a needle at a depth to deliver medicament to the upper 3 mm of a skin surface, comprising:
    an inner hub, configured to be adhesively secured to a skin surface;
    an outer hub, configured to be adhesively secured to a skin surface, and wherein said outer hub is configured to enclose said inner hub; and
    a flexible tube, for flexibly coupling said inner hub with said outer hub and providing a fluid communication path therebetween,
    wherein said outer hub is connected to said inner hub solely through said flexible tube, and wherein said inner hub is adhesively secured to said skin surface using a first adhesive layer that is separate from a second adhesive layer securing said outer hub to said skin surface.

10. An inserter, comprising:
an inserter button, and a lower inserter housing slidably coupled with said inserter button and configured to be rigidly coupled with an outer hub of an infusion set;
a hammer releasably secured within said lower inserter housing;
a spring, captured between said inserter button and said hammer;
a table, configured to rotationally secure an inner hub of said infusion set and configured to be struck by said hammer, wherein said inserter button is configured to release said hammer to strike said table and drive said infusion set for placement at an infusion site.

11. An inserter as recited in claim 10, wherein said table is configured to releasably secure said inner hub in a retracted position within said outer hub.

12. An inserter as recited in claim 10, wherein:
said table comprises a first detent; and
said inner hub comprises second detent, wherein said first detent is configured to rotationally engage with said second detent to releasably secure said table with said inner hub.

13. An inserter as recited in claim 12, wherein:
said outer hub comprises a third detent; and
said lower inserter housing comprises a fourth detent, wherein said third detent is configured to rotationally engage with said fourth detent to releasably secure said inserter with said outer hub.

14. An inserter as recited in claim 10, wherein said spring is configured to place said infusion set at a controlled rate of speed, preferably greater than 3.3 ft/sec. (1.0 m/sec.).

15. A method targeting a desired depth to deliver content to an upper skin surface, comprising the steps of:
placing an infusion device upon an infusion site and pressing an inserter button of said infusion device to release a hammer and spring to strike a table of said infusion device;
striking said table of said infusion device, said table releasably coupled with an infusion set of said infusion device, to move a needle of said infusion set of said infusion device into said infusion site a controlled rate of speed; and
removing said inserter button, hammer and spring, and table, from said infusion set.

16. A method targeting a desired depth to deliver content to an upper skin surface, comprising the steps of:
placing an outer hub of an infusion device upon an infusion site and pressing an inserter button of said infusion device to move a needle of an inner hub of said infusion device into said infusion site, wherein said needle is driven into said infusion site at a controlled rate of speed; and
removing said inserter button from said infusion device, wherein said inner hub is fully enclosed by said outer hub, and is connected to said outer hub solely through a flexible tubing after removal of said inserter button from said infusion device.

17. An infusion set inserter, comprising:
an inserter housing comprising an inner member and an outer member,
at least a portion of said outer member being displaceable relative to said inner member to activate the inserter,
said inner member releasably secured to an infusion set and being configured to prevent, prior to activation, displacement in an insertion direction of said infusion set receivable by said housing;
a ballistic hammer movably disposed within the inserter housing; and
a spring, captured between and contacting said outer member and said ballistic hammer;
wherein said outer member is configured to activate the device by releasing said spring and said ballistic hammer to strike said inner member which thereafter begins to drive said infusion set in said insertion direction for placement at an infusion site.

18. The inserter as recited in claim 17, wherein said infusion set comprises a patient cannula and an adhesive for adhering said infusion set to a patient's skin.

19. The inserter as recited in claim 18, wherein said inner member supports said infusion set in an initial position spaced apart from a patient's skin prior to activation.

20. The inserter as recited in claim 17, wherein said ballistic hammer selectively moves between a pre-activated position, in which the ballistic hammer does not contact the infusion set, and an activated position.

21. The inserter as recited in claim 20, wherein said spring biases the ballistic hammer toward the activated position prior to activation.

22. The inserter as recited in claim 20, wherein during at least part of the travel of said infusion set from an initial position to a position in which said patient cannula is inserted in the patient's skin, the ballistic hammer does not contact said infusion set.

23. The inserter as recited in claim 17, wherein said outer member comprises an activation button.

24. The inserter as recited in claim 17, wherein said infusion set comprises an intradermal infusion set.

25. A method of inserting a cannula of an infusion set into a patient's skin, the method comprising:
placing an inserter housing carrying an infusion set over an intended infusion site, said housing comprising an inner member and an outer member with said inner member releasably secured to said infusion set for preventing displacement in an insertion direction of said infusion set prior to activation; and
displacing at least a portion of said outer member relative to said inner member to activate the inserter, said activation comprising:
releasing a spring captured between and contacting said outer member and a ballistic hammer movably disposed within said inserter housing; and
driving said ballistic hammer with the force of said spring toward said inner member which thereafter begins to drive said infusion set in said insertion direction for placement at the intended infusion site.

26. The method as recited in claim 25, wherein said infusion set comprises an intradermal infusion set.

27. An insertion device assembly, comprising:
an infusion set; and
an inserter comprising:
an inserter housing comprising an inner member and an outer member, at least a portion of said outer member being displaceable relative to the inner member, the inserter housing supporting said infusion set in an initial position spaced apart from a patient's skin prior to activation, said infusion set including a patient cannula and an adhesive for adhering said infusion set to a patient's skin;
a ballistic hammer slidably disposed within the inserter housing to move between a pre-activated position and an activated position; and a spring disposed within the inserter housing and biasing the ballistic hammer toward the activated position prior to activation;

wherein displacement of the at least portion of the outer member activates the inserter, causing the ballistic hammer to move between the pre-activated position and the activated position under the force of the spring toward said infusion set and thereafter begin to impart momentum to said infusion set; and wherein during at least part of the travel of said infusion set from the initial position to a position in which said patient cannula is inserted in the patient's skin, the ballistic hammer does not contact said infusion set.

28. The insertion device assembly as recited in claim 27, wherein said biasing element is disposed between and contacts said outer member and said ballistic hammer.

29. The insertion device assembly as recited in claim 27, wherein said infusion set comprises an intradermal infusion set.

* * * * *